United States Patent [19]

Bertoncini

[11] Patent Number: 5,318,413
[45] Date of Patent: * Jun. 7, 1994

[54] PERISTALTIC PUMP AND METHOD FOR ADJUSTABLE FLOW REGULATION

[75] Inventor: Joseph Bertoncini, Gaithersburg, Md.

[73] Assignee: Biomedical Research and Development Laboratories, Inc., Gaithersburg, Md.

[ * ] Notice: The portion of the term of this patent subsequent to Mar. 24, 2009 has been disclaimed.

[21] Appl. No.: 856,758

[22] Filed: Mar. 24, 1992

Related U.S. Application Data

[63] Continuation of Ser. No. 518,996, May 4, 1990, Pat. No. 5,098,261.

[51] Int. Cl.⁵ .............................................. F04B 43/08
[52] U.S. Cl. .................................. 417/475; 417/474; 417/476; 417/477 R; 604/153
[58] Field of Search ............... 417/474, 475, 476, 477; 92/13.2; 604/153

[56] References Cited

U.S. PATENT DOCUMENTS

| | | | |
|---|---|---|---|
| 4,347,778 | 9/1982 | Murray | 417/475 |
| 4,648,812 | 3/1987 | Kobayashi et al. | 417/477 |
| 4,715,786 | 12/1987 | Wolf et al. | 417/22 |
| 4,798,590 | 1/1989 | O'Leary et al. | 417/477 |
| 4,834,630 | 5/1989 | Godwin | 417/477 |
| 5,011,378 | 4/1991 | Brown et al. | 417/474 |
| 5,098,261 | 3/1992 | Bertoncini | 417/475 |

FOREIGN PATENT DOCUMENTS

| | | |
|---|---|---|
| 0293081 | 11/1988 | European Pat. Off. |
| 2162943 | 7/1972 | Fed. Rep. of Germany |
| 2415417 | 10/1974 | Fed. Rep. of Germany |
| 3247313 | 6/1984 | Fed. Rep. of Germany |
| 8806138 | 8/1988 | PCT Int'l Appl. |

*Primary Examiner*—Richard A. Bertsch
*Assistant Examiner*—Alfred Basichas
*Attorney, Agent, or Firm*—Breneman & Georges

[57] ABSTRACT

A peristaltic pump is provided having an adjustable flow regulation provided by an adjustable axial elongation means for the variable elongation of resilient tubing disposed between the associated rotors of a rotary peristaltic pump or the plurality of reciprocal pushers or fingers in a linear peristaltic pump to provide a radial compression of successive sections of the resilient tubing. The rotary or linear peristaltic pump includes a calibrated display and a variable speed electric motor having forward and reversing capabilities along with computer interface control for precisely metering and monitoring the volume of liquids for medical, biological and laboratory applications. Individual adjustable flow regulation is provided for each of the resilient tubes in the peristaltic pump by providing for the independent adjustable elongation of the flexible tubing in relation to the plurality of reciprocal pushers or fingers in the linear peristaltic pump or the associated rollers in a rotary peristaltic pump in combination with a means for ascertaining and displaying the speed of the drive motor.

18 Claims, 9 Drawing Sheets

PERISTALTIC PUMP AND METHOD FOR ADJUSTABLE FLOW REGULATION

This application is a continuation of application number 07/518,996, filed May 4, 1990, now U.S. Pat. No. 5,098,261.

BACKGROUND OF THE INVENTION

1. Field of the Invention

The present invention pertains to peristaltic pumps and is applicable to linear peristaltic pumps and rotary peristaltic pumps having a section of resilient tubing disposed in between rollers or reciprocal fingers or pushers which progressively radially compress sections of the tubing to pump liquids. More particularly, the present invention pertains to linear and rotary peristaltic pumps which not only radially compress successive sections of resilient peristaltic pump tubing but also axially elongate the peristaltic Dump tubing with an adjustable tensioning means to elongate the peristaltic pump tubing to precisely control the cross sectional configuration of the tubing to adjust the flow rate of fluid pumped through the tubing in combination with a means for determining and displaying the speed of the motor operating thee peristaltic pump.

The novel linear and rotary peristaltic pumps constructed in accordance with the invention are particularly applicable to peristaltic pumps having a plurality of flow lines for precisely metering sample liquids to a plurality of samples in a precise and metered volume that are pumped by a peristaltic pump of a linear or rotary peristaltic pump design. The adjustable flow regulation in combination with the display or means for monitoring the speed of the drive motor is particularly advantageous in individually adjusting each of the peristaltic pump flow lines to precisely calibrate a predetermined flow rate or volume from each of the peristaltic pump flow lines to make certain each flow line delivers the same precise metered volume of fluid from each of the flow lines by the individual axial tensioning of each of the peristaltic pump tubing lines and for modifying the rate of flow by varying the speed of a variable speed motor means for driving the peristaltic pump. The axial tensioning of the tubing in conjunction with the speed of a variable speed electric motor imparts important adjustable flow regulation for the precise metering of fluids for applications in medical, biomedical and laboratory applications that require the precise metering and control for the delivery of fluids.

DESCRIPTION OF THE PRIOR ART

The prior art includes a wide variety of peristaltic pumps which have proved valuable in medical, biomedical and laboratory applications. Peristaltic pumps have been employed particularly advantageously in applications where low contamination and aeration are important considerations and have utilized two basic designs the linear design such as represented by Hemingway, et al, U.S. Pat. No. 4,893,991 and Cannon U.S. Pat. No. 4,728,265 and the rotary peristaltic pumps represented by Tangeman, U.S. Pat. No. 3,403,631, Soderquist, et al U.S. Pat. No. 4,886,431 and Kling U.S. Pat. No. 3,172,367. In both the linear and rotary peristaltic pump designs a section of resilient peristaltic pump tubing is radially compressed along successive sections to provide a pumping action. The linear and rotary peristaltic pump operate upon much the same principal of radial compression propagating axially to transfer and pump fluid from one end of the resilient peristaltic pump tubing to the other end.

The prior art has provided considerable attention in rotary and linear peristaltic pumps to the efficiency of the radial compression of the resilient peristaltic pump tubing with little or no consideration being given to the axial elongation or adjustment to the resilient peristaltic pump tubing to precisely control the amount of fluid being pumped through the peristaltic pump tubing by positioning the ends of the peristaltic pump tubing and providing an axially adjustable elongation means at one or both ends of the section of peristaltic pump tubing to provide for the individual axial elongation of the peristaltic pump tubing between the plurality of reciprocal pushers or fingers or the associated rollers in the rotary peristaltic pump. The prior art has further not provided a display means for carefully monitoring pump motor speed in relation to an axially adjustable elongation means for individually controlling the cross sectional configuration of the peristaltic pump tubing to precisely control the metering and flow of fluid delivered by the peristaltic pump.

In linear peristaltic pumps such as Cannon, U.S. Pat. No. 4,728,265 and Hemingway, et al 4,893,991 a great amount of attention is directed to the radial compression axially along the section of peristaltic tubing without consideration to an axial adjustment of the peristaltic tubing to precisely control the metering of fluids. Considerable attention is similarly given in the design of rotary peristaltic pumps to the radial compression forces exerted on the peristaltic pump tubing by providing various means for adjusting the axial tension exerted on the tubing in the peristaltic pump to vary the radial compressibility of the tubing with little or no consideration given to the axial elongation of the tubing to precisely control flow.

The most pertinent peristaltic pumps prior art appears to be Tangeman, U.S. Pat. No. 3,403,631 which provides levers for indiscriminately tensioning or relaxing all of the peristaltic pump tubing between periods of use and nonuse which indiscriminately elongates all of the tubing at the same time. Tangeman, U.S. Pat. No. 3,403,631 further provides a slot and screw device to permit for the compensation of the permanent stretch which may develop in the tubing after prolonged use but this tensioning device also provides for the substantially indiscriminate elongation of all of the peristaltic pump tubing as opposed to individual elongation and adjustment of each member of the peristaltic pump tubing to control the cross sectional configuration of each member of the tubing to provide for the precise metering or flow of fluids as is done in accordance with the present invention. Tangeman U.S. Pat. No. 3,403,631 further does not provide a display or means for calibrating the elongation of each tube in relation to a particular pump motor speed. Similarly, Kling, U.S. Pat. No. 3,172,367 provides an adjustment for tensioning the peristaltic tubing with respect to the associated rollers of a rotary peristaltic pump but like tangeman 3,403,613 does not individually adjust the axial elongation of each of the peristaltic tubing members to control cross sectional configuration to precisely meter fluids in combination with a pump speed display or monitoring means. As a result, Kling, like Tangeman, does not provide a precise control for the metering of precise volumes of fluid as is done in accordance with the present invention.

Other peristaltic pump prior art such as Ballentine, U.S. Pat. No. 3,402,673 provides a constriction of the ends of the peristaltic tubing to modify flow but does not provide for individually controlling the cross sectional configuration of the tubing by the axial elongation of the tubing to precisely control flow. The peristaltic pump in Thompson U.S. Pat. No. 4,906,168 similarly does not provide a means for axially elongating and adjusting the tension along the length of tubing in the peristaltic pump to precisely meter and deliver precise volumes of liquid pumped through the peristaltic pump. Soderquist, et al U.S. Pat. No. 4,886,431 provides an individual adjustable cartridge assembly for each member of the peristaltic pump tubing but the adjustment provided is for individually increasing and decreasing the radial deforming of the tubing as opposed to the axial elongation and deformation of the peristaltic pump tubing along the length of the peristaltic pump tubing to precisely meter and control flow provided by the peristaltic pump.

As a consequence of the importance of precisely controlling the volume of fluid metered and the control of rate of flow in peristaltic pumps, numerous designs and efforts have been provided in the prior art for constricting, occluding or otherwise providing adjustment for the radial pressure exerted on the peristaltic pump tubing which has not produced an effective, efficient means for metering the precise quantities of small amounts of fluid in peristaltic pumps. In most cases were small accurate quantities of fluid required metering syringes, pipettes and other volumetric or gravimetric devices have been utilized. Despite the importance of peristaltic pumps to medical, biomedical and laboratory applications, prior art peristaltic pumps have not effectively provided a precise metering or control of the flow of fluids with occlusion, constriction or other radial adjustment or control of the peristaltic pump tubing in prior art peristaltic pumps.

The present invention in contrast provides superior control for the precise metering and control of fluids by providing for the axial elongation of the peristaltic pump tubing to control the cross sectional configuration of the peristaltic pump tubing together with a precise monitoring and control of the speed of the peristaltic pump motor which provides far superior metering and flow control characteristics in view of the area upon which control forces are exerted. In a normal peristaltic pump tubing, the cross section of the tubing is small in comparison to the length of the tubing for which the axial elongation adjustment provide a far more sensitive, accurate and precise control of the metering and flow of fluids through the peristaltic pump tubing than can be accomplished through the radial adjustment or occlusion provided in the prior art to vary the radial compressive forces between the plurality of reciprocal pushers or fingers of the linear peristaltic pump or the associated rollers of the rotary peristaltic pump.

As a consequence of the minute variations in the uniformity of the peristaltic pump tubing in internal diameter, tubing wall thickness and resiliency characteristics along the length of the peristaltic pump tubing in conjunction with wear and use it has been difficult to precisely control and meter fluids in peristaltic pumps in critical chemical, biological, medical and laboratory applications which require precise metering of fluids. The axial elongation and adjustment provided by an adjustable tensioning device such as a screw thread process provides for the individually and infinitely adjustable tensioning of the peristaltic pump tubing to provide a precise control of the metering of fluids for use with peristaltic pump tubes of small, internal diameters in linear and rotary peristaltic pumps.

The adjustable axial tensioning means for individually elongating each length of peristaltic pump tubing in combination with the display or other means for controlling the speed of the peristaltic pump motor provides an effective metering system for delivering precise quantities of fluid by controlling the cross sectional configuration of each length of peristaltic pump tubing. The novel arrangement provides a system for the accurate calibration of peristaltic pumps constructed in accordance with the present invention to provide a precise control over the rate of flow in each of the hoses so as to provide a precise metering of fluids in biological, chemical, medical and laboratory uses.

SUMMARY OF THE INVENTION

The disadvantages and limitations of prior art peristaltic pumps including the problem of precisely regulating the flow for individual peristaltic pump tubing flow lines and individually adjusting and calibrating a plurality of peristaltic pump flow lines driven by a common radial deformation means can be obviated by the utilization of one or more means for longitudinally adjusting the tension of the peristaltic pump tubing disposed between the plurality of reciprocal pushers or fingers in linear peristaltic pumps or the associated rollers in the rotary peristaltic pumps. The advantages of the present invention are further augmented by the use of a display together with a precise means for controlling the speed of the peristaltic pump motor.

The axial tensioning of the peristaltic pump tubing in combination with the adjustability of the axial tensioning in combination with a variable speed peristaltic pump motor provides for important calibration and the precise metering control over the volume of liquid flowing through the peristaltic pump tubing and provides a wide range of control for individually changing or modifying the volume of fluids metered by the peristaltic pump. The precise fluid control provided by the individually adjustable peristaltic tubes to modify flow rate can be connected to a computer for the precise metering of fluids through the peristaltic pump for auto analysis and medical, biological, chemical and laboratory applications.

The novel peristaltic pumps constructed in accordance with the invention provide a superior peristaltic pump by concentrating on the fundamental aspects of peristaltic pumps which are the peristaltic pump tubing and providing significant control over the adjustment of the flow characteristics and pumping action of the peristaltic pump by a combination of the radial compression and axial tensioning of the peristaltic pump tubing to change the cross sectional configuration of the peristaltic pump tubing to provide a sensitive flow regulation for fluids flowing through the peristaltic pump. The axial tensioning of the individual tubing members of the peristaltic pump increases the sensitivity and efficiency of the peristaltic pump by providing for a more sensitive elongation adjustment of the individual peristaltic pump tubing to increase the efficiency of the action of the rollers or fingers upon the tubing while providing a means for compensating for variations in the internal hose diameter, the wall thickness, elasticity and age of the peristaltic pump.

The elongation or axial stretching of the individual peristaltic tube members together with the display means for accurately detecting and displaying the speed of the peristaltic pump motor provides an accurate and reliable means for compensating for variations in tube size, wall thickness and diameter and the action of the individual rollers against the walls of the tube in the pumping action to provide minute control of volumes of liquid delivered through novel peristaltic pumps constructed in accordance with the invention. The control provided by the peristaltic pumps of the present invention is so precise and minute as to be capable of controlling flow rates or equalizing flow rates in the peristaltic pump lines so minute as to be ordinarily incapable of measurement by volumetric means. The quantities precisely metered in peristaltic pumps of the present amount to the size of a small drop of liquid that in many cases is so small as to not be measured in the meniscus of volumetric measurements. The amounts of liquid controlled in accordance with the present invention many times are so small as to be measured only by gravimetric analysis.

The peristaltic pump tubing in the preferred embodiment includes two collars disposed at predetermined positions on the peristaltic pump tubing. The distance between the collars or restraining means depends upon the resilient composition of the material used in the peristaltic pump tubing, the inside diameter of the tubing, and the wall thickness of the peristaltic pump tubing. The two collars of the peristaltic pump tubing are disposed at a distance from one another such that a minimum amount of distance is maintained between the two collars so that the rotor provides a closing of the peristaltic pump tubing in the top dead center position of the radial compression means and such that additional tensioning on the peristaltic pump tubing does not substantially change the cross section diameter of the tubing from a circular cross section to an oval cross section that would otherwise significantly impede flow. Thereafter, the adjustable axial elongation means for tensioning the peristaltic pump tubing can be axially adjusted by a threaded process means to more precisely control the diameter of the peristaltic pump tubing to provide an extremely accurate and reliable delivery of liquid from each of the individually adjustable tubes of the peristaltic pump. The adjustable axial elongation means can be utilized to assist in calibration of the novel peristaltic pumps constructed in accordance with the invention by allowing travel and adjustment from opened and closed positions in relation to the rollers of a rotary peristaltic pump.

DESCRIPTION OF THE DRAWINGS

Other advantages of the invention will become apparent to those skilled in the art from the following detailed description of the invention in con)unction with the accompanying drawings in which.

DETAILED DESCRIPTION OF THE INVENTION

The adjustable volume of flow by axially elongating the peristaltic pump tubing through the peristaltic pump mechanism by adjusting volume by changing the tension on the peristaltic pump tubing and modifying flow rate by increasing or decreasing the motor speed in accordance with the present invention is applicable to a wide variety of peristaltic pumps including the traditional rotary peristaltic pump with associated rollers or linear peristaltic pumps having a plurality of reciprocal pushers or fingers.

Figure 1:
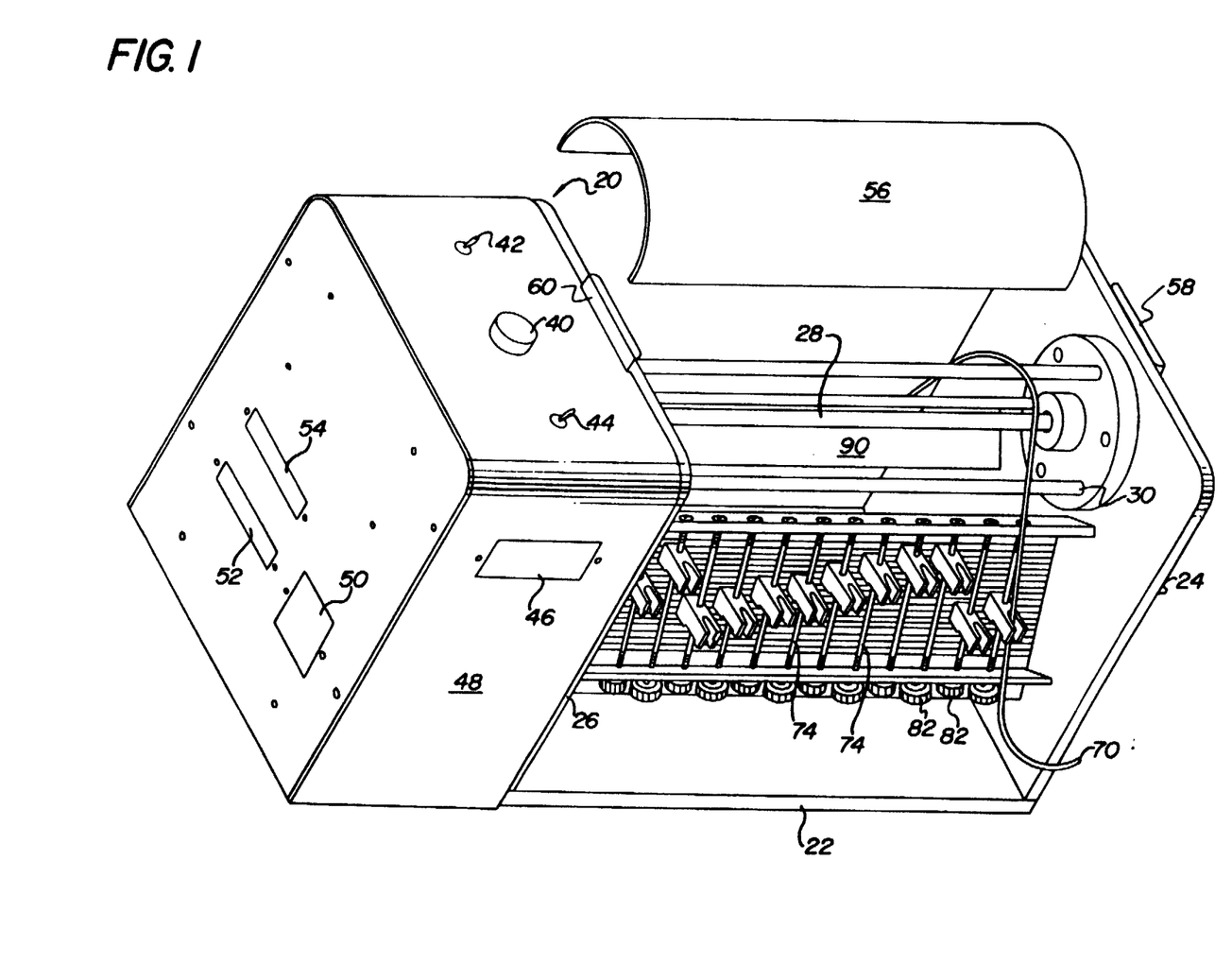
FIG. 1 is a perspective partially exploded view of a rotary peristaltic pump constructed in accordance with the present invention.
Figure 2:
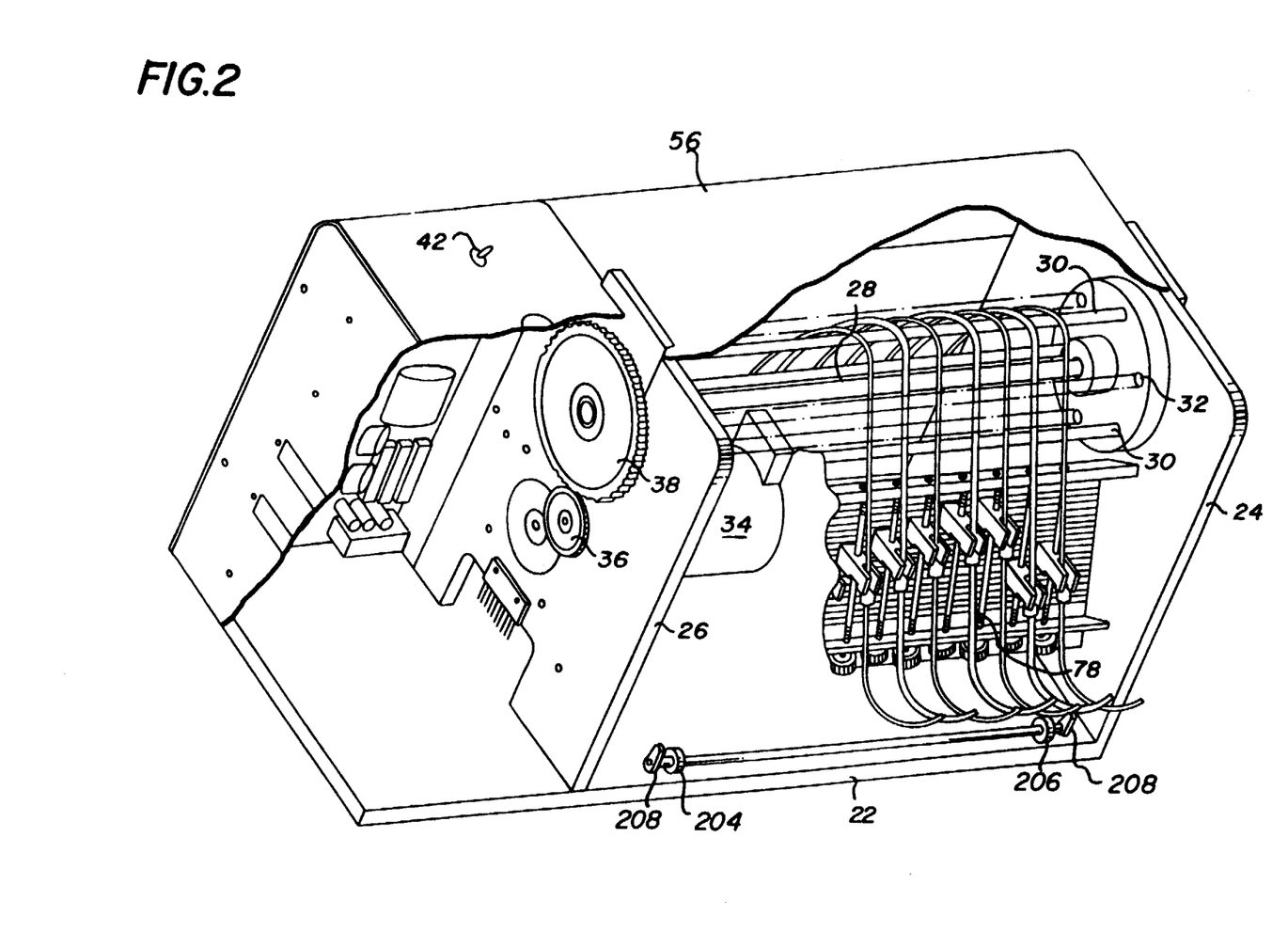
FIG. 2 is a perspective view of the peristaltic pump of FIG. 1 without the protective cover partially cut away to illustrate various electrical components of the novel peristaltic pump.

Referring now to FIG. 1, a novel peristaltic pump 20 is illustrated having a base 22 with supporting stands 24, 26 for supporting a rotor 28 having a plurality of peristaltic pump rollers 30. In the preferred embodiment, the peristaltic pump rotor 28 includes six or more rotatable peristaltic pump rollers 30 which are free to rotate at either end in bearings 32 to provide peristaltic pumping action upon rotation of the rotor 28. Referring now to FIGS. 1, 2, 3 and 4, the rotation of the rotor 28 is provided by an electric motor 34, powered by a power supply card KEPCO FAW12-4.2 which is geared to the rotor 28 through gear 36 and gear 38 connected to rotor 28. In the preferred embodiment, electric motor 34 is a variable speed motor controlled by a driver chip from SPRAGUE UDR2 878w or UDn2879w and a variable speed power adjustment which may be manually controlled through multi-position rheostat 40 and can rotate clockwise or counterclockwise by the activation of switch 42. A further four-position switch 44 may be utilized to turn the motor 34 on, off or manually or auto position to allow the variable speed motor 34 to be turned on, off, operated manually or automatically via a computer which will be described hereinafter in greater detail. A digital panel meter 46 is provided in the housing 48 which may or may not include a motor contained within the housing. The housing 48 further includes an outlet 50 which may operate on 110 or 220 standards for European or U.S. electrical supply together with a standard computer interface 52 which is compatible with PC computers to drive the pump with a computer to turn it on or off automatically when switch 44 is placed in the automatic mode. The computer interface 52 may be an RS 232 standard computer interface or other computer interface for interfacing with various types of computers. In addition, a screw strip 54 is provided for wire interface with other than a PC, RS 232 computer. The electronics for interfacing with the computer are shown in FIG. 1 and FIG. 2 and are available from Intensil ICL-232.

An optional cover 56 which may be of plexiglass or opaque material may be utilized as a protective cover held in place by clips 58 and 60 to prevent injury to laboratory personnel. The motor 34 is a brushless stepping motor such as available from Motor Superior electro M062-LS03 or M062-CS03 which is utilized in accordance with the preferred embodiment since such motors are not interfered with by electrical current and charges from the computer that prevent false signals to the computer and thereby sacrifice the accuracy of the precise flow meter control provided by peristaltic pumps constructed in accordance with the present invention.

Referring now to FIGS. 1, 2, 3 and 4, novel rotary peristaltic pumps constructed in accordance with the invention are illustrated in which one or more sections of peristaltic pump tubing 70 are disposed between a fixed finger 72 and then adjustable finger mechanism 74 for axially stretching or elongating and infinitely varying the tension on peristaltic pump tubing 70. Each peristaltic pump tubing 70 is separately adjusted and tensioned by its own adjustable finger mechanism 74 which as shown in FIGS. 1 through 4 employs a U-shaped bracket 76 having a screw 78 with an adjustable finger 80 traveling up and down screw 78 in response to actuation of the adjustment knob 82. The adjustment knob 82 allows individual adjustment for each of the peristaltic pump tubing 70 by separately actually elongating and modifying, the circular internal diameter of the tubing to adjust the volume of liquid pumped through the peristaltic pump by rollers 30 in the rotation of rotor 28.

Figure 3:
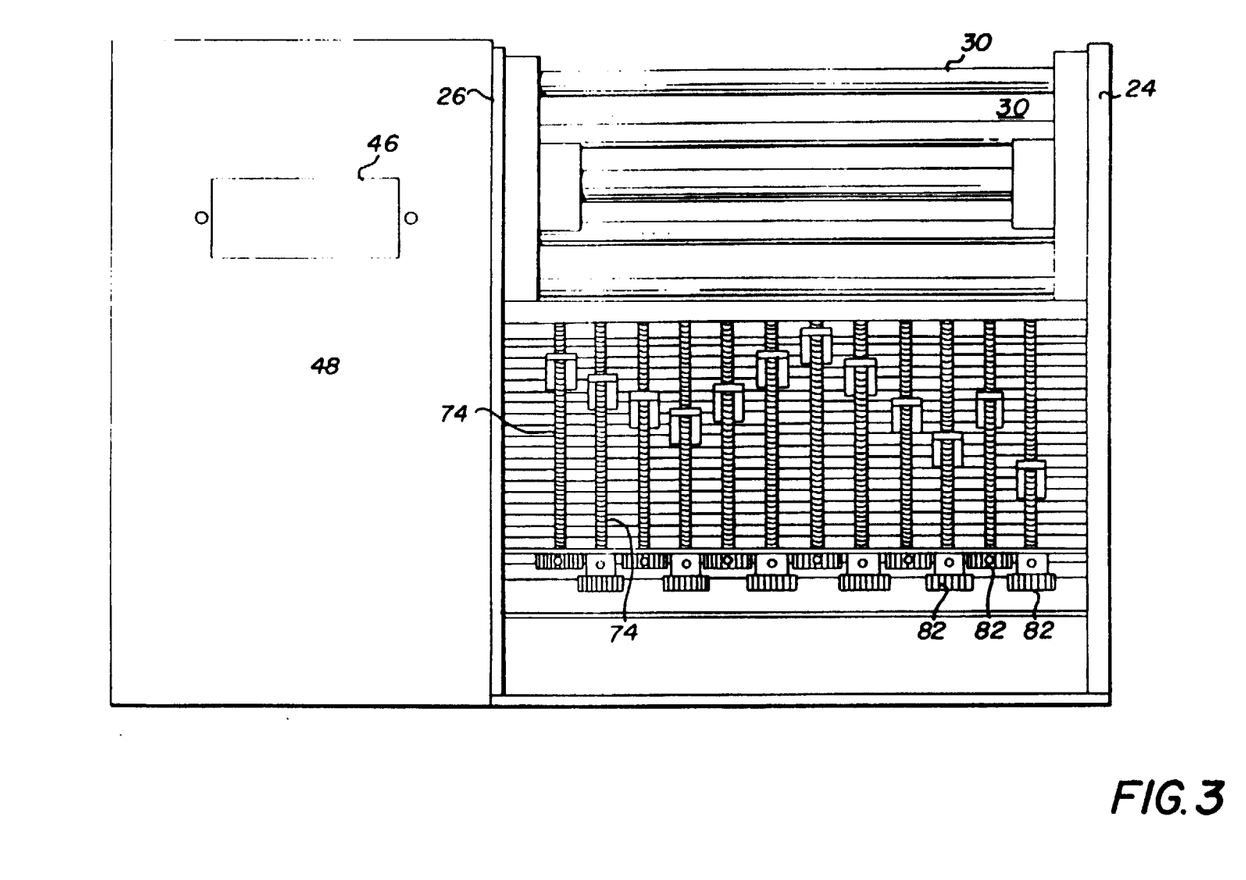
FIG. 3 is a front-side elevational view of the rotary peristaltic pump of FIG. 1.
Figure 4:
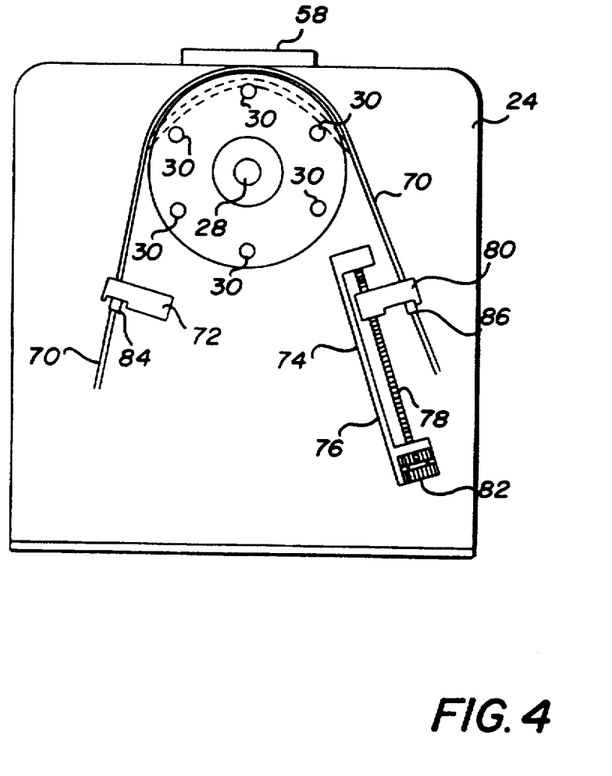
FIG. 4 is a partially cut away side elevational view of the peristaltic pump of FIG. 1.

Peristaltic pump tubing 70 may be constructed of any resilient material and may be natural such as rubber or synthetic as the case in Neoprene or other elastomeric materials. Resinous or synthetic resinous materials such as teflon, natural rubber, tygon or silicon may be used. In the preferred embodiment, a silicon rubber tube such as available from Flourocarb is utilized having an internal diameter of 1/16, ⅛ or 1/32 of an inch for transporting fluids through the peristaltic pump tubing 70. Peristaltic pump tubing 70 is anchored at one end to a fixed finger 72 by a collar 84 which may be glued or otherwise fixed or fastened to peristaltic pump tubing 70. At the other end of peristaltic tubing 70, a further collar 86 is provided which may like collar 84 be glued or fastened to peristaltic pump tubing 70 to fix peristaltic pump tubing in a tensioned relationship with respect to the rotary peristaltic pump rollers 30 or the reciprocating fingers of a linear peristaltic pump. In normal operation with adjustable finger 80 moved to the top most position, the peristaltic pump tubing 70 should, in the preferred embodiment of the invention, be slightly tensioned from between fixed finger 72 and adjustable finger 80. The distance between collars 84 and 86 in a silicon tubing of about a 1/16 of an inch is about 8 to 14 inches as is available form Flourocarb to provide a minimal deformation of the cross section of tubing 70 toward the oval cross section. More particularly, it is desirable in accordance with the present invention to, in the least tensioning on the tubing, to provide a substantially circular cross section in peristaltic pump tubing 70 that is not subjected to the action of rollers 30. Thereafter, the travel provided by gear 38 should be anywhere from one to six inches for tensioning peristaltic pump tubing 70 which may upon further tensioning actually change the cross sectional configuration from a circular cross section to an oval cross section. The individually adjustable adjustments means is provided for each peristaltic pump tubing 70 which may include 12 separate peristaltic pump tubing 70 adjustable means as is shown in FIG. 3 or may include 20 or more peristaltic pump hose tubing, each having its own separate adjustable finger mechanism 74 where a plurality of peristaltic pump tubing lines are desired. Each adjustment knob 82 may be provided in a staggered arrangement such as shown in FIG. 3 or may be provided on alternating sides of the fixed finger side or adjustable-finger side across the axial length of rotor 28.

The individual adjustment for tensioning peristaltic pump tubing 70 across the rollers of the peristaltic pump provides far greater control in the modification of the volume of flow than does a radial adjustment for squeezing or constricting or occluding the peristaltic pump tubing to flow. The length between the collars 84 and 86 is important in relation to the type of material selected for peristaltic pump tubing 70, the inside diameter of the peristaltic pump tubing 70 and the wall thickness of the peristaltic pump tubing 70. In accordance with the preferred embodiment of the invention, the cross section of the peristaltic pump tubing 70 by the actuation of adjustment knob 82 to adjust the tension on peristaltic pump tubing 70 maintains a predominantly circular cross section on the peristaltic pump tubing 70 that is not in contact with the peristaltic pump rollers or reciprocating fingers. As is illustrated in FIG. 3, each of the peristaltic pump tubing 70 which may be of the same wall thickness and diameter is provided with its own individual peristaltic tube tensioning adjustable finger mechanism 74. In this manner, the individual idiosyncracies of each section of peristaltic pump tubing can be controlled to a degree of less than the size of a drop of liquid in each of the peristaltic pump tubing 70 by compensating for the imperfection and differences in this internal diameter, wall thickness and elasticity characteristics of the same tubing by separately tensioning each of the tubes so that an identical flow rate can be achieved in each of the tubes of the peristaltic pump. In addition, the individually adjustable peristaltic pump tubing 70 can be calibrated and re-calibrated after each use to maintain a constant volume delivery at a particular motor speed to make certain the tubes deliver a predetermined quantity throughout the life of the peristaltic pump tubing 70. In addition, peristaltic pump tubing 70 can be easily replaced by simply opening protective cover 56 and installing a new section of tubing between the fixed finger 72 and the adjustable finger 80 and thereafter re-calibrating the machine to obtain a particular desired flow at a particular rpm as displayed in the digital panel meter 46 to calibrate that particular peristaltic pump tube to deliver a predetermined quantity or volume of liquid by adjusting the tension on the adjustable finger for particular peristaltic pump tube.

Figures 5, 6, 7:
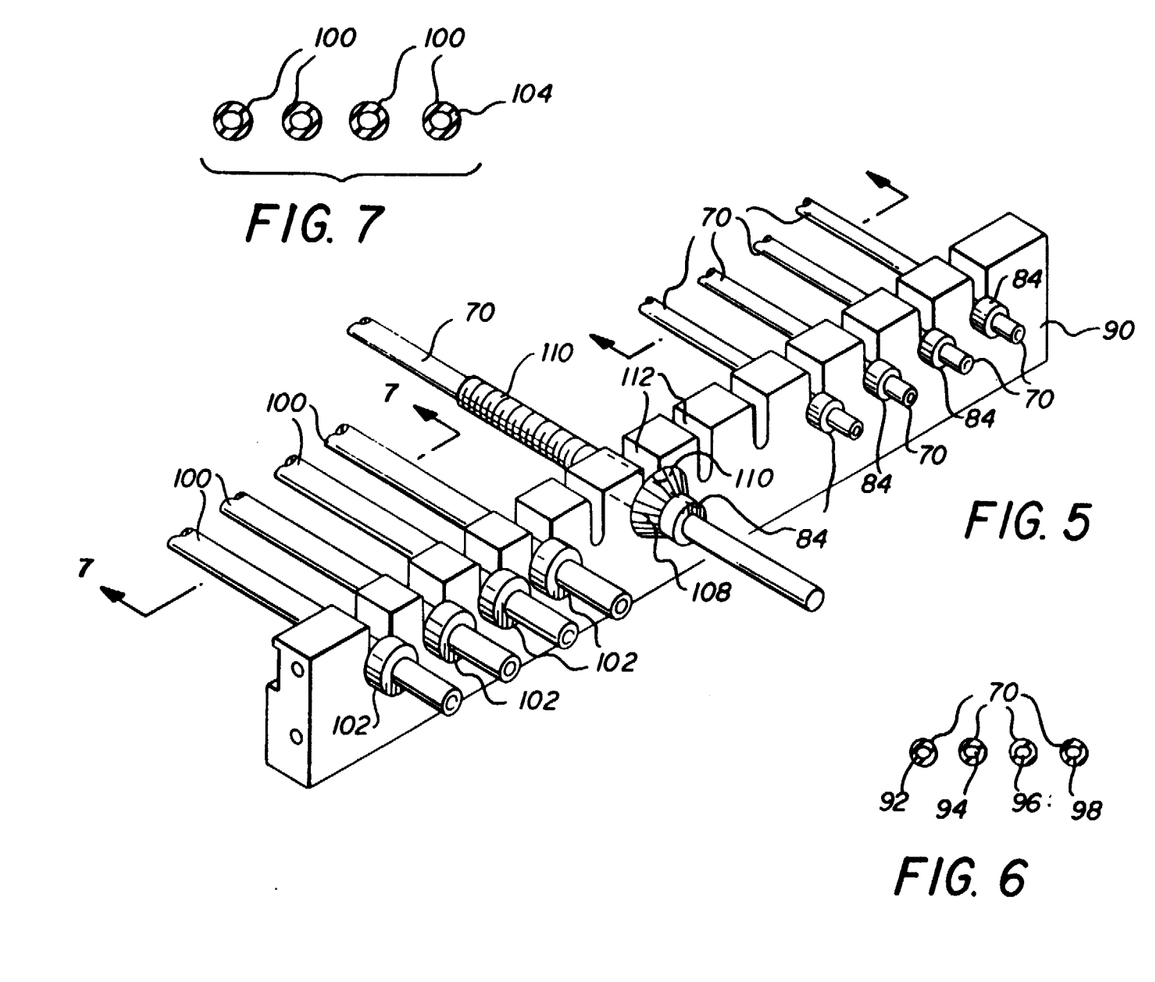
FIG. 5 is a perspective view of a positioning means for securing one end of peristaltic pump tubing illustrating various size tubing and alternative embodiments for providing adjustable axial elongation means for peristaltic pump tubing.
FIG. 6 is a view of one set of peristaltic pump tubing taken along the line 6—6 of FIG. 5.
FIG. 7 is a view taken along the line 7—7 of a different size of peristaltic pump tubing taken along the line 7—7 of FIG. 5.

Referring now to FIG. 5, a fixed rack 90 is illustrated as is utilized for fixing one end of the peristaltic pump tubing 70 in place. Fixed rack 90 as well as peristaltic pump 20 can employ a plurality of peristaltic pump tubing 70, have the same internal diameter and wall thickness made of the same elastomeric material with restraining collar 84 and 86. The tensioning of each of the tubing 70 by each of the individual tensioning adjustable finger mechanism 74 produces a cross section of tubes as shown in FIG. 6 which, for purposes of illustration, illustrates a varying tension on each of the peristaltic pump tubing 70 with slight variations resulting in the internal diameters 92, 94, 96 and 98 which, depending upon the relationship of the wall thickness of the tube and degree of tension, not only results in a decrease in the circular diameter as between tubing 70, but also results in a slight modification of the tube to an oval cross sectional configuration.

Tubing 70 may all be of the same internal diameter and outside cross section or may be of the same internal diameter and different wall thickness. In the case where wall thicknesses are varied, tension is similarly varied with the adjustable finger mechanism 74 to provide a desired flow rate calibration. In addition, different flow rates may be achieved by utilizing tubes of different internal diameter such as represented by tubes 100 in fixed rack 90. Tubes 100 having a different wall thickness and internal diameter may be utilized to provide channels of increased flow and pumping action even though the same speed of electric motor 34 is used to turn rotor 28. In the case of tubes 100, collars 102 restrain each of the tubes 100 in fixed rack 90 and individual tensioning adjustable finger mechanism 74 are utilized to increase individually the tension on each of the peristaltic tubes 100 while individual tensioning means is provided to individually tension each of the tubing 70 in fixed rack 90. The individual tensioning of peristaltic pump tubes 100 with each having its own separate adjustable finger mechanism 74 for tensioning each of the tubes 100 individually in fixed rack 90. The tensioning of tubes 100 which have a thinner wall thickness 104 than the wall thicknesses 106 in relation to the internal diameters of peristaltic pump tubing 70 provide a more oval shaped cross section when taken along the line 7—7 as illustrated in FIG. 7. The more oval openings in wall thickness 106 of tubes 100 provide important advantages in controlling the volume of fluids pumped through the peristaltic pump and peristaltic pump tubing in relation to a predetermined speed of motor 34 as reflected by digital panel meter 46.

Figure 8:
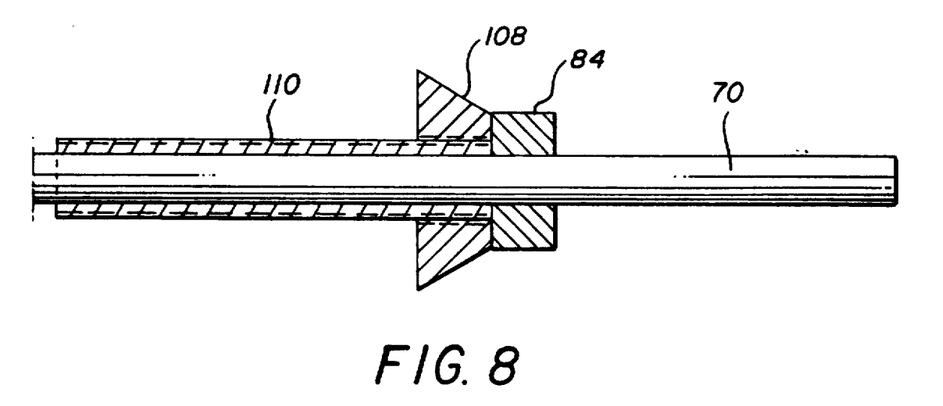
FIG. 8 is a side elevational view of a further alternative for providing adjustable axial elongation means in combination with positioning means of FIG. 5.
Figure 14:
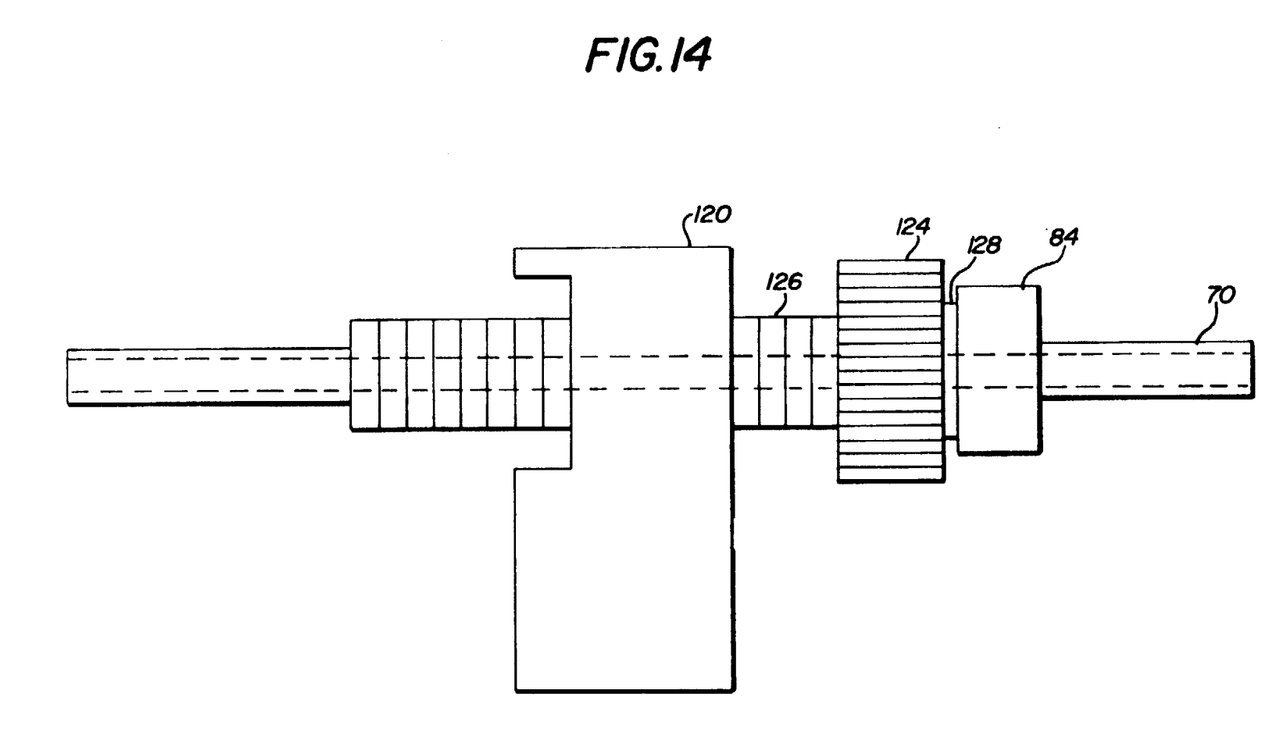
FIG. 14 is a further embodiment of a means for adjusting the flow rate of the peristaltic pump tubing by axially elongating the peristaltic pump tubing through the peristaltic pump mechanism.
Figure 15:
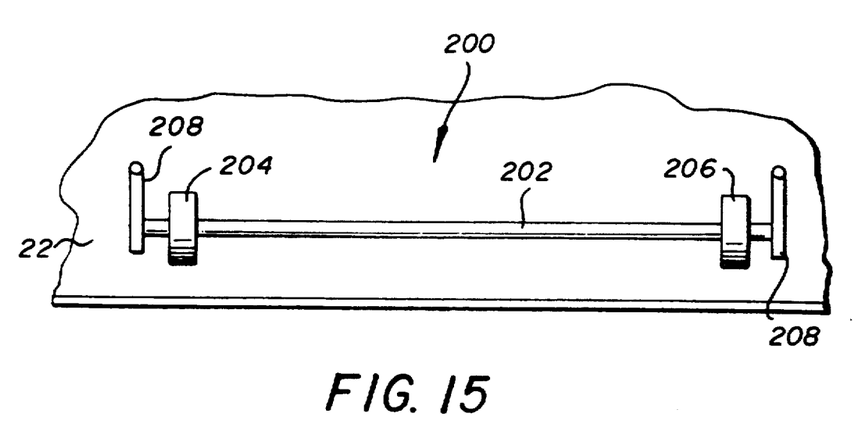
FIG. 15 is a section of FIG. 2 illustrating a means for measuring and positioning collars on the peristaltic pump tubing.

In a further alternative embodiment of the invention, fixed rack 90 may be provided with an adjustable means for adjusting the tension of the tubing 70 alone or in combination with adjustable finger mechanism 74 to axially elongate tubing 70 in the peristaltic pump 20. The means for elongating peristaltic pump tubing 70 can utilize a knurled knob 108 threadably engaged to a collar 110 extending across the slot 112 in rack 90. The knurled knob 108 abuts against a collar 84 provided in tubing 70 and by turning knurled knob 108 against the flat surface 114 of rack 90, advances collar 110 which abuts collar 84 to stretch tubing 70. Alternatively, the tensioning means as shown in FIGS. 5 and 8 may be modified as illustrated in FIG. 14 to include a fixed finger 120 which threadably engages a knurled nut 124 having a threaded tube 126 for threadable engagement in advancement in fixed finger 120. The other end of knurled nut 124 abuts against collar 84 or 86 of peristaltic pump tubing 70 for axially elongating peristaltic pump tubing 70 and adjusting the flow of fluid pumped through the peristaltic pump through peristaltic pump tubing 70. A rotatable bearing collar 128 can be provided between knurled nut 124 and collar 84 to prevent the twisting of peristaltic pump tubing 70 upon the adjustment of knurled nut 124.

The individually adjustable flow volume to meter fluids through a peristaltic pump is equally applicable to both rotary peristaltic pumps and linear peristaltic pumps which pump fluid through a resilient tube where the rate of flow is dependent upon the speed of the peristaltic pump motor and the volume is precisely controlled through the axial elongation of the peristaltic pump tubing with the adjustable flow rate means of the present invention.

Figure 9:
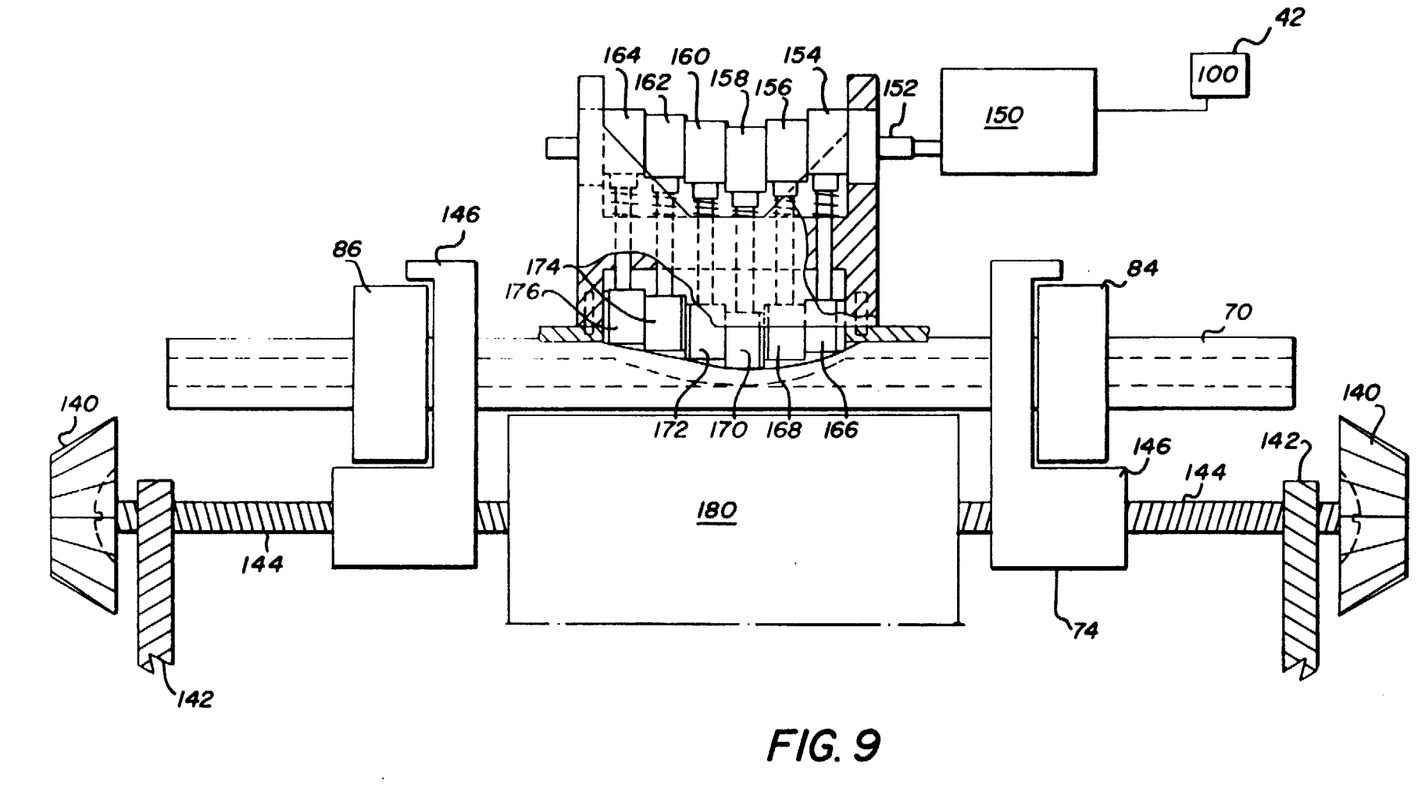
FIG. 9 is a side elevational view schematically illustrating a linear peristaltic pump providing a variable flow rate adjustment constructed in accordance with the present invention.

Referring now to FIG. 9, the utilization of a linear peristaltic pump constructed in accordance with the present invention is illustrated in which a peristaltic pump tubing 70 includes a collar 84 and 86 with an individually adjustable finger mechanism 74 having a knurled nut 140, a fixed support 142 for maintaining the spaced relationship between the fixed support 142 and the nut 140 and a threaded portion 144 disposed in a moveable assembly 146 threadably engaged to knurled nut 140 so that rotation of knurled nut 140 precisely controls the tension on peristaltic pump tube 70 through peristaltic tube collar 84. In the preferred embodiment, collar 86 may also include a moveable assembly 146 which may be activated by a similar knurled nut 140 having a support 142, a threaded portion 144, and a moveable assembly 146. The linear peristaltic pump constructed in accordance with the present invention further includes a variable speed motor 150 for rotating a shaft 152 having a plurality of cams 154, 156, 158, 160, 162, and 164 for activating a plurality of linear fingers 166, 168, 170, 172, 174, and 176 for successively compressing sections of peristaltic pump tubing 70 in a sinusoidal configuration to pump fluid through peristaltic pump tubing 70. A support 180 opposing fingers 166 to 176 provides for the successive radial compression of successive sections of peristaltic pump tubing 70 to pump fluid through the peristaltic pump. The adjustable tensioning means for axially adjusting the axial tension and elongation on peristaltic pump tubing 70 in accordance with the present invention, carefully controls the volume of fluid through peristaltic pump tubing 70 while the rate of fluid is dependent upon the speed of motor 150 in the activation of fingers 166-176. The precise metering of fluid in peristaltic pump tubing 70 can be controlled by the elongation of peristaltic pump tubing 70 in the manner heretofore described so that even a portion of a drop of fluid can be precisely measured which might not otherwise be detected volumetrically but could be detected by weighing the amount of fluid delivered through the peristaltic pump tubing 70. The linear peristaltic pump tubing 70 also includes a digital panel meter 46 for displaying the speed of the pump motor 150 to assist in the accurate calibration of the peristaltic pump having an adjustable means for axially elongating the peristaltic pump tubing 70 to accurately control the volume of fluid being pumped through the peristaltic pump.

Figures 10, 11:
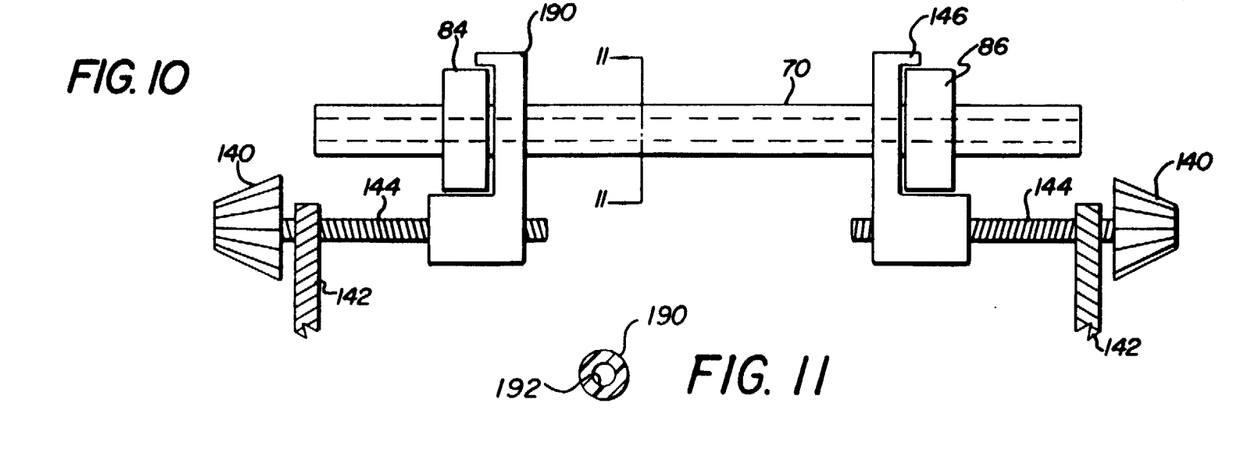
FIG. 10 is a schematic view of an alternative means for axially elongating the peristaltic pump tubing illustrating the peristaltic pump tubing in a slightly tensioned arrangement.
FIG. 11 illustrates the peristaltic pump tubing taken across the line 11—11 of FIG. 10.
Figures 12, 13:
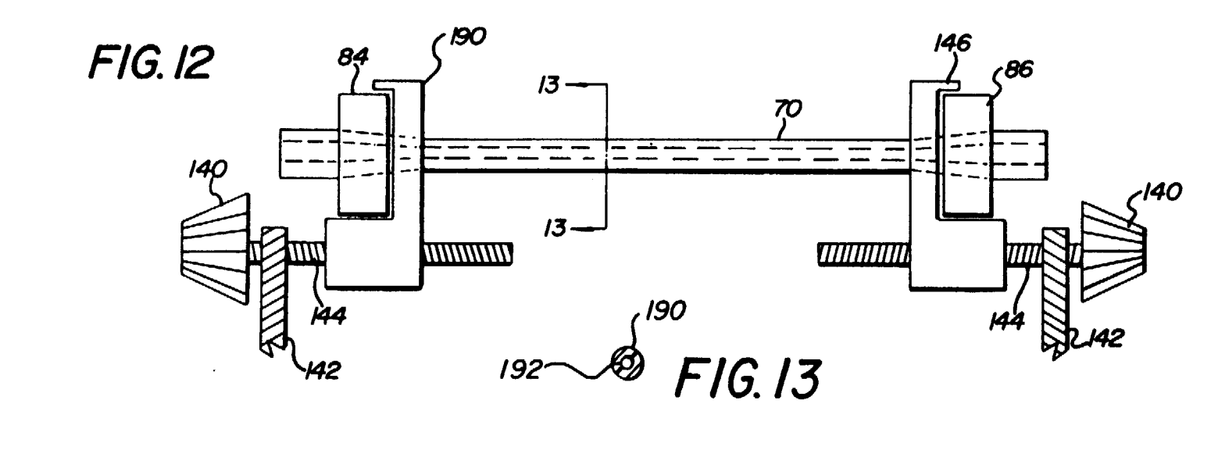
FIG. 12 is a schematic view similar to FIG. 10 illustrating the peristaltic Dump tubing in one of a variable axially adjustable elongation tensioning for adjusting the volume of flow through the peristaltic pump tubing.
FIG. 13 is a section of the peristaltic pump tubing taken across the line 13—13 of FIG. 12.

Referring now to FIGS. 10, 11, 12, and 13, the arrangement between the adjustable means and the peristaltic pump tubing is illustrated in relation to the cross sectional diameter of the tubing. In FIG. 10, a section of peristaltic tubing 70 is illustrated having collars 84 and 86 is illustrated schematically. In FIGS. 10-14, the rollers and reciprocal pushers or fingers have been eliminated for the purposes of illustration. The rotary rollers or fingers are disposed between the moveable assembly 146 and the stationary or moveable member 190 for axially elongating the peristaltic pump tubing 70 as it is being radially compressed by the action of the rollers or peristaltic pump fingers. The elongation of the peristaltic pump tubing 70 in cooperation with the action of the peristaltic pump fingers or rollers precisely controls the tension and action by the peristaltic pump on the peristaltic pump tubing to deliver precise measured quantities of fluid through the peristaltic pump. In FIG. 10, a section of peristaltic pump tubing in a substantially relaxed configuration is illustrated in which the distance between the collars 84 and 86 is about 10 inches pounds for a peristaltic pump tubing made of Silicon having a internal diameter of about 1/16 of an inch and a wall thickness of about 3/16 of an inch. The cross sectional relationship is illustrated in FIG. 11 wherein the wall 190 is under tension and the internal diameter 192 is of a substantial cross sectional configuration. The adjustment of peristaltic pump tubing 70 is illustrated in FIG. 12 in which the tube has been stretched for purposes of calibration such that the wall thickness 190 as shown in FIG. 13 has decreased in diameter resulting in a subsequent decrease in diameter in the internal diameter 192 of peristaltic pump tubing 70. It is believed that a slight degree of oval cross section configuration is achieved at diameter 192 and that this oval cross section configuration increases with a decrease in the wall thickness of the peristaltic pump tubing 70. It is believed that the best advantages in accordance with the present invention are achieved by axial elongation of the tubing during pumping such that the substantially cylindrical tube remains of a substantial cylindrical cross section configuration during the stretching. It is believed that tubing that is actually elongated that significantly changes from a cylindrical to an oval cross section does not provide the significant advantages of adjustment that are achieved through peristaltic pump tubing that retains a more cylindrical configuration. It is therefore believed that wall thickness of the peristaltic pump tubing should not be particularly thin as it sacrifices control over the peristaltic pump tubing resulting from the axial elongation of the tubing in relation to the action of the fingers or rollers of the peristaltic pump. It will be recognized that a number of important factors are involved in the design of a peristaltic pump including the wall thickness of the peristaltic pump tubing which cannot be so thick as to impede the action of the rollers or peristaltic fingers or plungers in the axial compression of the peristaltic pump tubing in combination with the resiliency of the elastomeric material from which the peristaltic pump is composed. These factors of resiliency, wall thickness, internal diameter and also uniformity of wall thickness and internal diameter to the peristaltic pump tubing are all important in precisely metering, regulating, and controlling the action of the peristaltic pump. The novel adjustments provided in accordance with the present invention for elongating axially the length of the peristaltic pump tubing to compensate for some of the factors of imperfection in internal diameter and wall thickness are important in order to achieve precise control of liquids flowing through the peristaltic pump tubing particularly as the tubing ages after repeated use. The invention contemplates variation in the tubing due to age, lack of uniformity, and lack of material construction by calibrating each of the tubes individually to precisely control the amount of fluid metered through the peristaltic pumps constructed in accordance with the present invention.

Referring now to FIGS. 2 and 16, a tube measuring device 200 is illustrated which includes a tubing slot 202 having a collar positioning indentation 204 and 206 for gluing and positioning collars 84 and 86 on the peristaltic pump tubing 70. In addition, a pair of clips 208 may be provided for holding the ends of peristaltic pump tubing 70 while the collars 84 and 86 are glued in place in the recesses or collar positioning indentations 204 and 206.

The novel peristaltic pumps constructed in accordance with the present invention provide a precise metering and control by the utilization of a digital display to indicate the speed of the motor for purposes of calibration and to provide an infinitely but finely controlled axially elongation of the peristaltic pump tubing to precisely meter quantities of fluid through the peristaltic pump tubes. The peristaltic pump constructed in accordance with the present invention in the preferred embodiment contemplates the utilization of stainless steel and teflon bearings for the purposes of reducing friction and for the purposes of preventing the change in diameter of the tubing in the operation of the peristaltic pump. The reversible peristaltic pump motor is capable of delivering an accurate flow of fluids in both directions and is susceptible to automated or computer control by the utilization of an RS 232 interface for a standard PC computer to drive the pump motor when the switch is placed in an automatic position to engage the computer. All of the parts of the novel peristaltic pumps are constructed of stainless steel or aluminum to prevent deterioration and the peristaltic pump tubing is in the preferred embodiment silicon peristaltic pump tubing and surgical grade tubing for purposes of uniformity and calibration with sections of pump tubing being easily replaceable where substituted with other tubing in the course of the service life or operational requirements of the novel peristaltic pumps constructed in accordance with the present invention.

The method of the present invention contemplates the utilization of a peristaltic pump providing axial compression of a resilient tubing member to provide peristaltic pumping action in combination with a means for simultaneously elongating the peristaltic pump tubing to specific axial adjustments to modify or change the volume of flow of fluid through the peristaltic pump. In accordance with the present invention, individual sections of tubing can be calibrated to deliver precise quantities of liquid or, where multiple tubing is utilized, each of the channels or ports can be individually calibrated to maintain a precise volumetric control of fluid for use in auto analysis, medical, surgical, biological and laboratory and chromatographic analysis of various compositions.

The novel design of the present invention provides a precise control for the metering of fluids utilizing peristaltic pumps by allowing the calibration of the machine together with a digital display to illustrate the speed of the motor and precisely control the calibration of the volume of fluid going through the peristaltic pump. The individual adjustment of each of the tubes to the peristaltic pump and its elongation to control the volume compensates for differences in individual tubes as a result of internal diameter variations, peristaltic tube wall thicknesses, and lack of uniformity of the elasticity of the tubing material itself by allowing independent adjustment means to stretch each of the tubes independently to calibrate a particular desired flow from each of the tubes.

As will be recognized by those skilled in the art, the present invention has a wide range of applicability to various types of laboratory and chemical analysis in the laboratory for chromatography and precise analytical analysis where the precise metering of fluids is desired and in biological and biochemical assays and equipment where precise metering of fluids is required. The peristaltic pumps of the present invention are also, in view of the precise handling of and metering of fluids, are useful in biological and medical fields and in surgical operations requiring the precise metering of fluids or administration of drugs during various types of surgical procedures.

As a result, the invention may be implemented in a variety of ways utilizing the precise metering control achieved by the cooperation of the action on the axial compression of sections of peristaltic tubing using peristaltic pump means in combination with the axial elongation provided by individual adjustment and tensioning of the peristaltic pump tubing. It will be further appreciated the present invention may be adapted in a number of different ways to provide varying fluid flow rates by utilizing tubes of different diameters while at the same time precisely monitoring and controlling and calibrating the flow rates through each of the tubes utilizing the axial elongation of the tubing to precisely calibrate the machine in relation to the speed of the peristaltic pump operating motor which may be digitally displayed and controlled or controlled through the utilization of a computer. It will be further appreciated that the present invention may be implemented and modified in a variety of ways to suit the particular application of the peristaltic pump to a particular medical, biological, or laboratory procedure. Consequently, it is intended that these and other modifications and applications of the invention to a variety of laboratory, medical, and biological applications may be made within the scope and spirit of the invention as defined in the following claims.

What is claimed is:

1. A peristaltic pump for metering minute quantities of fluid comprising:
   (a) resilient peristaltic pump tubing having a first end and a second end;
   (b) radial deforming means for radially deforming successive sections of said peristaltic pump tubing disposed intermediate said first end and said second end of said peristaltic pump tubing;
   (c) positioning means for securing said first end of said length of peristaltic pump tubing on one side of said radial deforming means;
   (d) adjustable axial elongation means disposed on the other side of said radial deforming means at a location remote from said positioning means for axially elongating said length of peristaltic pump tubing disposed intermediate said second end and said radial deforming means; and
   (e) a motor means for operating said radial deforming means and a display means for indicating the speed of said motor means.

2. The peristaltic pump of claim 1 further comprising a plurality of peristaltic pump tubing and a plurality of adjustable axial elongation means for separately axially adjusting said plurality of peristaltic pump tubing.

3. The peristaltic pump of claim 2 wherein said plurality of peristaltic pump tubing have different inside diameters.

4. The peristaltic pump of claim 1 wherein said motor means is an electric brushless stepping motor.

5. The peristaltic pump of claim 4 wherein said electric brushless stepping motor is a variable speed motor.

6. The peristaltic pump of claim 5 wherein said variable speed electric brushless stepping motor includes means for operating said motor in forward and reverse.

7. The peristaltic pump of claim 4 further comprising a computer or microprocessor for operating said electric brushless stepping motor.

8. The peristaltic pump of claim 1 wherein said positioning means is an opening in a support member of the peristaltic pump in combination with a collar disposed around said peristaltic pump tubing.

9. The peristaltic pump of claim 8 wherein said positioning means includes a second adjustable axial elongation means disposed in said opening.

10. The peristaltic pump of claim 9 wherein said second adjustable axial elongation means is a threaded tube disposed around said peristaltic pump tubing adjacent to said collar in combination with corresponding threads provided in said opening.

11. A linear peristaltic pump for metering and delivering precise quantities of fluid comprising:
   (a) at least one resilient peristaltic pump tubing having a first end and a second end;
   (b) a radial deforming means for radially compressing successive sections of said peristaltic pump tubing disposed intermediate said first end and said second end of said resilient peristaltic pump tubing;
   (c) positioning means disposed on one side of said radial deforming means for receiving said first end of said peristaltic pump tubing;
   (d) an adjustable axial elongation means disposed at a location remote from said positioning means for axially elongating said peristaltic pump tubing to elongate and precisely adjust the cross sectional configuration of said peristaltic pump tubing; and
   (e) motor means for operating said radial deforming means and a display means for indicating the speed of said motor means.

12. The peristaltic pump of claim 11 wherein said motor means is an electric brushless stepping motor.

13. The peristaltic pump of claim 12 wherein said electric brushless stepping motor is a variable speed motor.

14. The peristaltic pump of claim 13 wherein said variable speed electric brushless stepping motor includes means for operating said motor in forward and reverse.

15. The peristaltic pump of claim 14 further comprising a computer or microprocessor for operating said electric brushless stepping motor.

16. A rotary peristaltic pump for metering and delivering precise quantities of fluid comprising:
   (a) at least one resilient peristaltic pump tubing having a first end and a second end;

(b) a plurality of rollers for radially compressing successive sections of said peristaltic pump tubing disposed intermediate said first end and said second end of said resilient peristaltic pump tubing;

(c) positioning means disposed on one side of said plurality of rollers for securing said first end of said peristaltic pump tubing;

(d) an adjustable axial elongation means disposed at a location remote from said positioning means for axially elongating said peristaltic pump tubing to elongate and precisely adjust the cross sectional configuration of said peristaltic pump tubing; and (e) motor means for operating said plurality of rollers and a display means for indicating the speed of said motor means.

17. The rotary peristaltic pump of claim 16 further comprising a plurality of peristaltic pump tubing and a plurality of adjustable elongation means for separately elongating each of said plurality of peristaltic pump tubing.

18. The rotary peristaltic pump of claim 17 wherein said motor means is a variable speed motor.

* * * * *